United States Patent [19]

Weeks

[11] Patent Number: Plant 6,457

[45] Date of Patent: Dec. 13, 1988

[54] ROSE PLANT NAMED 'PARTY TIME'

[76] Inventor: O. L. Weeks, 12610 Central Ave., Suite 76, Chino, Calif. 91710

[21] Appl. No.: 428

[22] Filed: Jan. 5, 1987

[51] Int. Cl.[4] ..... A01H 5/00

[52] U.S. Cl. ..... Plt./11

[58] Field of Search ..... Plt./11

*Primary Examiner*—Robert E. Bagwill
*Attorney, Agent, or Firm*—Vincent G. Gioia

[57] ABSTRACT

A new red blend hybrid tea rose.

1 Drawing Sheet

The present invention relates to a new and distinct variety of rose plant of the hybrid tea rose class, which was originated by my crossing as seed parent the rose known as "Perfume Delight" (U.S. Plant Pat. No. 3,282) and as pollen parent the rose known as "Half Time" (U.S. Plant Pat. No. 4,007). The denomination of this new rose is "Party Time".

Among the novel characteristics possessed by this new variety which distinguish it from its parents and all other varieties of which I am aware are its attractive, red and yellow colored flowers which change in tonality upon aging. The new variety is also attractive for the unique overall effect of the red-edged petals on an otherwise yellow rose, particularly in the ½ to full open stage before aging. This combination changes in many interesting ways throughout the aging process of the flower from the opening of the bud to the spent bloom. Asexual reproduction by budding of the new variety as performed in San Bernardino County, Calif., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Colour Chart (RHSCC). The terminology used in color description herein refers to plate numbers in the aforementioned color chart, e.g., "8A" is plate 8A of the Royal Horticultural Society Colour Chart.

Parentage: Seedling.
*Seed parent.*—"Perfume Delight".
*Pollen parent.*—"Half Time".
Class: Hybrid Tea.

The following observations are made of specimens grown outdoors in San Bernardino County, Calif. during the month of September.

FLOWER

Blooming habit: Recurrent.

A. Bud:
- (1) *Size.*—Medium.
- (2) *Form.*—Ovoid.
- (3) *Color.*—After sepals fall, bud coloring as seen on reverse side of petals first visible as a tight bud is Mimosa yellow to Canary yellow (near 8A to near 9A to near 11B) beginning at the point of petal attachment and extending upward until blending with Rhodonite red, 51A, at about ⅓ to ½ of petal length where red coloring washes into the yellow and then predominates at the petal edge.
- (4) *Sepals.*—About ½ of bud.
- (5) *Peduncle.*—Length — medium. Aspect — straight. Strength — erect, strong. Color — reddish green.

B. Bloom:
- (1) *Size.*—Average size when fully expanded — about 4½ to 5 inches.
- (2) *Borne.*—Primarily singly, one to a stem.
- (3) *Form.*—Center slightly depressed in bud form but as flower opens center petals are upright and remain so for the life of the bloom. Petals rolled outward. Petals are moderately ruffled.
- (4) *Petalage.*—Number of petals under normal conditions — about 50 to 55.
- (5) *Color.*—As petals unfurl, flower color character changes substantially from bud coloring. Petal top surface of outer petals is pronounced Neyron rose, 55A to near 51A at its deepest tonality toward petal edge thus lightening to near 55B and 55C toward petal base. However, yellow coloring is near point of petal attachment. Petal undersurface of outer petals continues yellow coloring but much paler than bud, near 11C to 11D, petal edges still display some red color washing. As flower opens, yellow coloring of inner petals appears deeper toned, near 11A, with less red coloring visible on inner petals except at petal edges. As flower ages, yellow coloring becomes near white and general tonality of aged flower is red and near white.

C. Petals:
- (1) *Texture.*—Thick.
- (2) *Appearance.*—Inside and outside are satiny.
- (3) *Form.*—Ovoid.
- (4) *Arrangement.*—Regularly arranged.
- (5) *Petaloids in center.*—Numerous.
- (6) *Persistence.*—Drop off cleanly.
- (7) *Fragrance.*—Medium.
- (8) *Lasting quality.*—About 5 days on plant; 3 to 5 days as cut flower.

REPRODUCTIVE ORGANS

A. Stamens, filaments and anthers:

*Arrangement and color.*—Irregularly arranged around styles. Color — very slight reddish overlay.

B. Pollen:

*Color.*—Medium yellow.

C. Styles: Short length, uneven.

D. Stigmas:

*Color.*—Greenish yellow.

E. Hips: None observed.

PLANT

A. Form: Upright and spreading.

B. Growth: Vigorous, uniform branching.

*Height attained.*—About 4 feet.

C. Foliage: Compound 5 leaflets.

(1) *Size.*—Medium.

(2) *Quantity.*—Abundant.

(3) *Color.*—New foliage: Upper side — greenish bronze. Under side — reddish bronze. Old foliage: Upper side — between 147A and 147B. Under side — between 146C and 146D.

(4) *Shape.*—Oval, pointed.

(5) *Texture.*—Upper side is smooth, dull and under side is dull.

(6) *Edge.*—Serrate.

(7) *Seration.*—Simple.

(8) *Leaf stem.*—Color — reddish green. Under side — dull green.

(9) *Stipules.*—Medium, rather heavily bearded.

(10) *Resistance to disease.*—Blackspot — none observed. Mildew — average. Rust — none observed.

D. Wood:

(1) *New wood.*—Color — between 138B and 138C with reddish overlay. Bark — smooth with many thorns.

(2) *Old wood.*—Color — reddish green. Bark — smooth.

E. Thorns:

(1) *Thorns.*—Quantity (main stalk) — numerous. On laterals from stalk — numerous. Form — long, narrow, pointed downward. Length — medium. Color — between 145A and 145B. Position — regular.

(2) *Prickles.*—Few to none.

F. Winter hardiness: Average.

I claim:

1. A new and distinct variety of rose plant of the hybrid tea rose class, substantially as shown and described, characterized particularly by red and yellow colored flowers changing in tonality upon aging, borne singly on strong, erect stems.

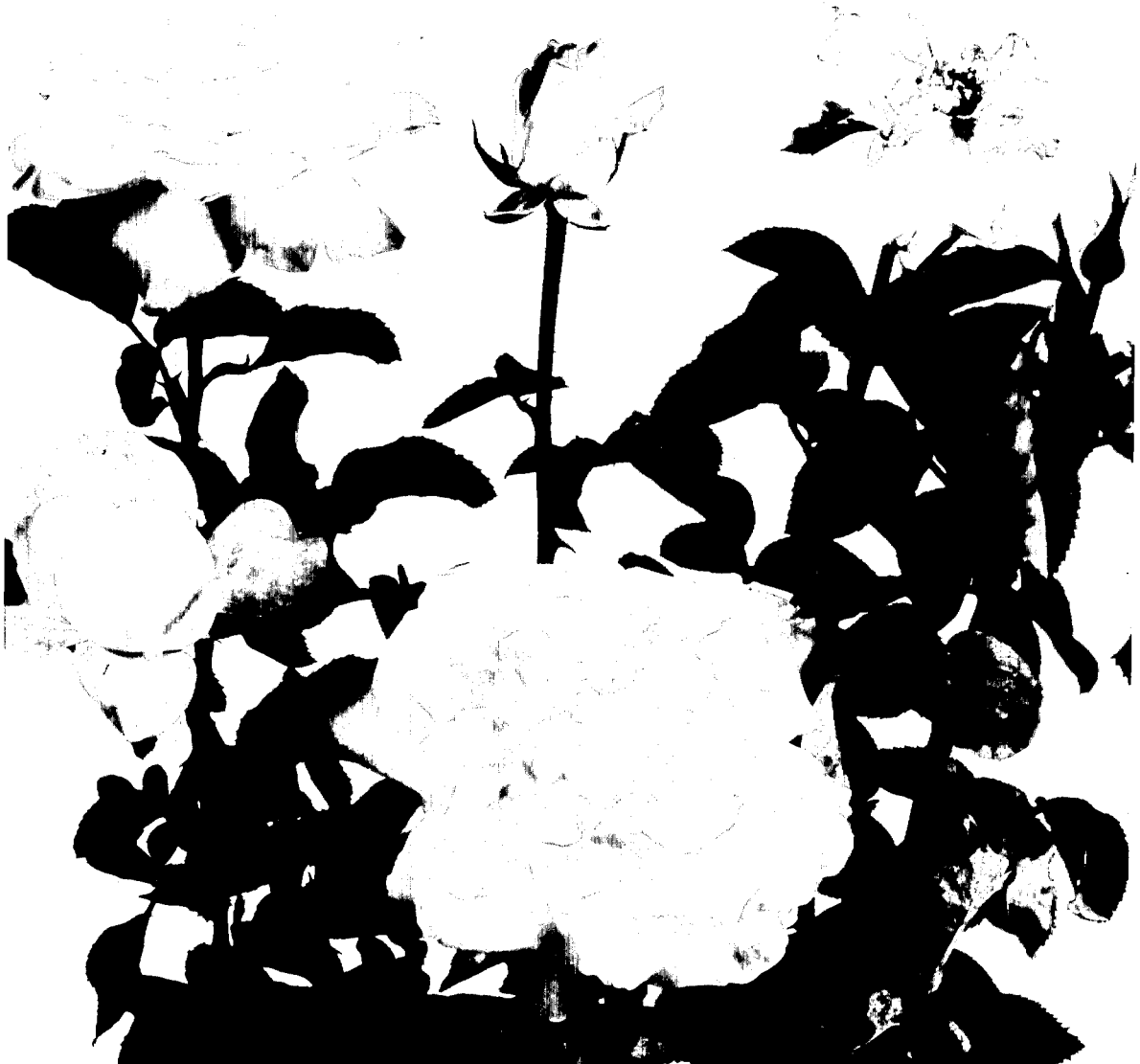

* * * * *